United States Patent [19]
Yagata et al.

[11] Patent Number: 4,982,735
[45] Date of Patent: Jan. 8, 1991

[54] ARTIFICIAL VENTILATOR

[75] Inventors: Kazuhiko Yagata, Kanagawa; Yasuo Noguchi, Yokohama, both of Japan

[73] Assignee: Sumitomo Bakelite Company Limited, Tokyo, Japan

[21] Appl. No.: 274,122

[22] Filed: Nov. 18, 1988

[30] Foreign Application Priority Data

Mar. 1, 1988 [JP] Japan .................................. 63-45941

[51] Int. Cl.$^5$ ............................................ A61M 16/00
[52] U.S. Cl. .......................... 128/204.23; 128/204.21; 128/30.2
[58] Field of Search ...................... 128/202.12, 205.26, 128/30, 30.2, 724, 204.21, 204.23

[56] References Cited

U.S. PATENT DOCUMENTS

| | | | |
|---|---|---|---|
| 2,466,108 | 4/1949 | Huxley, III | 128/30.2 |
| 2,581,893 | 1/1952 | Wilm | 128/30.2 |
| 2,588,192 | 3/1952 | Akerman et al. | 128/30.2 |
| 2,758,594 | 8/1956 | Huxley, III et al. | 128/30 |
| 2,759,474 | 8/1956 | Kling | 128/30.2 |
| 2,774,347 | 12/1956 | Emerson | 128/30 |
| 2,780,222 | 2/1957 | Polzin et al. | 128/30 |
| 2,825,327 | 3/1958 | Tunnicliffe | 128/30.2 |
| 2,853,998 | 9/1958 | Emerson | 128/30.2 |
| 3,333,581 | 8/1967 | Robinson et al. | 128/30.2 |
| 3,368,550 | 2/1968 | Glascock | 128/30.2 |
| 3,802,417 | 4/1974 | Lang | 128/724 |
| 3,903,869 | 9/1975 | Barcalari | 128/202.12 |
| 4,328,799 | 5/1982 | LoPiano | 128/205.26 |
| 4,448,189 | 5/1984 | Lasley | 128/205.26 |
| 4,474,571 | 10/1984 | Lasley | 128/205.26 |
| 4,481,938 | 11/1984 | Lindley | 128/205.26 |
| 4,621,621 | 11/1986 | Marsalis | 128/205.24 |
| 4,770,165 | 9/1988 | Hayek | 128/202.12 |
| 4,838,263 | 6/1989 | Warwick et al. | 128/30.2 |

FOREIGN PATENT DOCUMENTS

| | | |
|---|---|---|
| 61176348 | 1/1985 | Japan . |
| 61232861 | 4/1985 | Japan . |
| 6311133 | 7/1986 | Japan . |
| 6354167 | 8/1986 | Japan . |

OTHER PUBLICATIONS

The New England J. of Medinice, vol. 268, No. 2, pp. 61–68 (1963.1).
Respiration, vol. 6, No. 3, pp. 254–259 (1987).
Respiration and Circulation, vol. 34, vol. 4, pp. 407–411 (1986.4).
Respiratory Care, vol. 27, No. 3, 271–275 (1982).
Clinical Thoracic Surgery, vol. 4, No. 2, pp. 153–157 (1984.3).

*Primary Examiner*—Edgar S. Burr
*Assistant Examiner*—Aaron J. Lewis
*Attorney, Agent, or Firm*—Browdy and Neimark

[57] ABSTRACT

An artificial ventilator includes a dome for covering the precordial and the sides of the thoracoabdominal of a patient, a blower to be used for applying negative and positive pressures within the dome, a regulator for adjusting a pressure, and the like. The valve switching device is controlled by a respiration detection system. In the respiration detection system, a pyrolelectric element is used as a respiratory sensor for detecting a temperature change rate caused by an inspired and expired air flow. The temperature change rate signal obtained by the sensor is compared with a threshold value set by a variable resistor, the start timings of expired air and inspired air are detected in accordance with the comparison result, and air inspiration and expiration start timing signals are outputted. Further, the artificial ventilator can be provided with various functions of forced respiration and intermittent deep breathing by means of a timer, synchronization only with air inspiration timings, reduction of frequency of respiration assistance for the intention not to use the ventilator in the near future, backup during apnea, and the like. The artificial ventilator allows a physilogical respiration assistance matching the patient's physiological intention by synchronizing with the patient's respiration. Thus, an effort and pain in breathing with a conventional mechanical ventilation can be avoided so that the artificial ventilator is suitable for a long term use and useful for a quick recovery of respiration function of an acute respiratory failure patient.

10 Claims, 7 Drawing Sheets

ARTIFICIAL VENTILATOR

BACKGROUND OF THE INVENTION

The present invention relates to a ventilatory assister for various types of respiratory failure patients.

A negative pressure type artificial ventilator which assists physiological negative pressure respiration is useful for patients having chronic respiratory failure such as pulmonary fibris, pulmonary emphysema, secondary disease after pulmonary tuberculosis, etc., and for patients having neuromyopathy malady, or the like.

An extra thoraco-abdominal negative pressure artificial ventilator, or so-called iron lung was made in 1927 by Drinker, wherein a respiratory failure patient is laid within the dome the interior of which is then made negative in pressure to expand the thorax, inflate the lung and assist the respiration. However, the iron lung is volumious, heavy, immovable and inefficient. In the 1950's, a positive pressure artificial ventilator which sends oxygen via a tube inserted in the windpipe had been prevailing so that an iron lung became to be used scarcely.

In 1930's, another method of also expanding the thorax to assist respiration had been tried by mounting the dome only on the thoraco-abdominal. However, it was difficult to air-tightly contact the bottom peripheral portion of the dome for various patients whose posture are different each other. The efficiency thereof was inferior to that of an iron lung.

Recently, attention has been drawn to some disadvantage of a positive pressure artificial ventilator, particularly for chronic respiratory failure patients. Namely, such patients have a clear consciousness so that they feel a pain against endotracheal intubation used with the positive pressure artificial ventilator. In addition they can not eat food and have a conversation. Another disadvantage is that the lung may be damaged by the positive pressure, infectious disease via the windpipe may occur, and so on. Further, there is also a problem that since the patient has long relied upon the artificial ventilator, he or she cannot dispense with it after recovery, or the number of respiratory assistances becomes necessary to be reduced gradually over a long period.

In view of the above background, the negative pressure artificial ventilator has taken a favorable turn in the 1980's. An extra thoraco-abdominal negative pressure artificial ventilator has been developed, whose dome is made of a light material and can be attached to the patient body (e.g., refer to "Respiratory Care", 27(3), pp.217 to 275, 1982, "Clinical Thoracic Surgey", 4(2), pp.153 to 157, 1984, "Respiration and Circulation", 34(4), pp.407 to 411, 1986). The ventilators described in the above articles, however, are arranged to mechanically assist respiration by using a constant respiration timing. Therefore, the constant timing may mismatch the timing which a patient desires to have, so that a so-called fighting condition appears which hurts patient's feelings.

Also, a method of assisting respiration in accordance with a patient's spontaneous respiration has been made also for a negative pressure artificial ventilator, e.g., by picking up changes in pressure and temperature caused by respiration at the vicinity of the patient's narises (refer to "New Eng. J. of Med.", 268, 61, 1963, "Japanese Patent Laid-open Pulbication" JP-A-x61-176348, "Respiration", 6(3), 254, 1987). However, this respiration assistance does not always follow the patient's real physiological intention and is not practically realized up to date.

The method of assisting respiration in accordance with a respiration rhythm set in the conventional ventilator is none the less unnecessary because of the following reasons: For those patients with weak respiration from which the expiration and inspiration timings are difficult to be picked up, such as patients with neuromyopathy malady like myotonic dystrophy, and for those patients under apnea, it is requisite to carry out mechanical respiration assistance in accordance with the respiration rhythm previously set by the ventilator. Further, for those patients whose spontaneous respiration becomes feeble or who get into apnea because of a sudden change of patient's health condition, it is requisite to immediately change to respiration assistance by the respiration rhythm previously set by the ventilator.

SUMMARY OF THE INVENTION

It is an object of the present invention to provide, in the field of a thoraco-abdominal negative pressure artificial ventilator which conventionally cannot take synchronization with a respiratory timing of a patient, a negative pressure artificial ventilator which can assist physiological respiration matching a patient's physiological intention by picking up the patient's respiration.

According to one aspect of the present invention, the artificial ventilator comprises: a dome made of hard material, said dome having an opening at the apex thereof for connection to an air duct and a fitting made of elastic material at the bottom periphery thereof; a blower adapted to be connected to said air duct for sucking and exhausting air relative to said dome; an air suction duct and an air exhaustion duct adapted to connect said dome and said blower together; a negative pressure regulator mounted on an exhaustion piping system; a positive regulator mounted on a suction piping system; a pressure sensor for detecting a pressure within said dome; an exhaustion valve and a suction valve for controlling air exhaustion and suction; a release valve for releasing a negative or positive pressure into atmospheric air; a bypass valve for bypassing air when said air exhaustion valve or said air suction valve is closed; a valve switching device for controlling to open and close said air exhaustion valve, air suction valve, release valve and bypass valve; and a respiration detection system comprising a respiratory sensor including a pyroelectric element mounted at the passage of a respiration air or near the narises for detecting a temperature change rate at said passage or near said narises, and a respiration detection circuit for comparing a temperature change rate signal obtained by said pyroelectric element with a threshold value set at a variable resistor, detecting the start timings of expired air and inspired air in accordance with the comparison result, and outputting a timing signal, said respiration detection system controlling said valve switching device. The artificial ventilator is further provided with other system functions of forced ventilation by means of a timer, intermittent deep breathings, synchronization only with the timings of inspired air, reduction of frequency of respiration assistances after removal of the artificial ventilator, backup during apnea, and the like.

DESCRIPTION OF THE PREFERRED EMBODIMENTS

Figure 1:
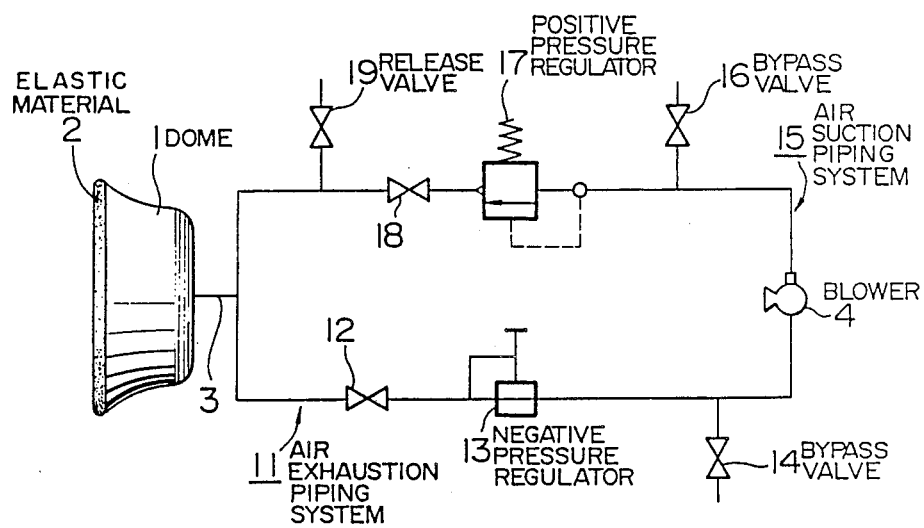
FIG. 1 is a schematic diagram of a piping system for sucking and exhausting air into and from the dome of the artificial ventilator according to the embodiment of the present invention.

A dome used with this invention has an outer shape as shown in FIG. 1 and is generally designated by reference numeral 1. The dome is used in such a manner that it is attached on the chest wall of a patient like a cuirass, and the interior thereof is made negative pressure to expand the patient thorax. Therefore, it is necessary for the dome to have a size and shape allowing to cover at least the precordia. It is more preferable that the size and shape can cover the abdomen and the sides of the thoraco-abdominal. The material of the dome is not particularly limited on condition that it is hard and non-deformable under application of negative or positive pressure in practical use. However, the material preferably has a high strength, and is relatively light, which includes: light metal such as aluminum alloy; laminated molds or reinforced plastics (FRP) made of thermo-plastics such as hard vinyl chloride resin, metaacrylic resin, polycarbonate resin, and polyamide resin pllychro, or made of thermo-setting plastics such as phenol resin, epoxy resin and unsaturated polyester resin; or carbon fiber reinforced plastics (CFRP).

The bottom periphery of the dome is provided with an elastic material 2 in order to tightly contact the body surface of a patient and prevent air leakage therefrom. The elastic material 2 is preferably natural rubber, synthetic rubber, various elastomers or their foamed material derived from styrene, olefine, polyester, polyurethane, polybutadiene or the like. If the foamed material is used, it is preferable to coat the surface of the material with soft resin such as urethane resin, vinyl chloride resin, vinyl acetate resin or the like. A tube made of above described various elastomers may be used as the elastic material 2. The tube may be filled in with high viscosity fluid such as liquid paraffin, ethylene glycol or the like, foamed material such as urethane spongy or the like, foamed beads made of such as polystyrene, polyethylene or the like. If the foamed beads are filled in, it is more preferable to exhaust air within the tube because beads in the tube are gathered together to thus allow to hold a specific outer shape of the tube and fitly align the bottom periphery with the patient's body form.

In order to carry out artificial ventilation with the aid of negative and positive pressure within the dome 1 of this invention, the air duct 3 is connected to the opening at the apex of the dome 1 to suck and exhaust air in and from the dome 1 with the blower 4. The blower 4 to be used with this invention has no particular limitation, but the air volume displacement in the order of 0.2 to 2.0 m$^3$/min is necessary to rapidly make the interior of the dome 1 negative pressure.

In order to raise the thorax by means of a negative pressure and assist respiration, it is necessary to reduce the internal pressure of the dome 1 down to $-10$ to $-50$ mm Hg, or preferably down to $-10$ to $-20$ mm Hg. Excessive negative pressure will give the patient uncomfortable feelings. In view of this, the negative pressure regulator 13 is disposed at the air exhaustion piping system 11 to adjust it while measuring the dome internal pressure with the pressure sensor, thus maintaining the dome internal pressure within the above-described range.

The present invention further presents a significant feature that not only the thorax is expanded by making the dome internal pressure negative during air inspiration of a patient, but also if necessary, the thorac is pushed down by making the dome internal pressure slightly higher than the atmospheric pressure during air expiration of a patient. In the latter case, it is also necessary to control the timings when a positive pressure is applied, the duration, strength and the like thereof. To avoid excessive positive pressure, the positive pressure regulator 17 is disposed at the air suction piping system 15 to regulate the pressure within the dome 1.

As appreciated from the foregoing description, the dome internal pressure is made to have a predetermined negative pressure rapidly after the start of patient's air inspiration and maintain the negative pressure during air inspiration and thereafter, it is released to the atmospheric pressure at the same time as the start of air expiration. In the case where a positive pressure is to be applied, the dome internal pressure reaches a predetermined positive pressure after a predetermined time from the start of air expiration and maintains the positive pressure for a predetermined period and thereafter, it is released to the atmospheric pressure, to thus complete one cycle at the next start of air inspiration.

A change of the dome internal pressure is measured with a pressure sensor or gauge, thus enabling to recognize air leakage from the dome bottom periphery or a dome internal pressure change suitable for particular disease. Obviously, the pressure change pattern may be outputted in analog signals, or displayed in digital signals.

Next, how the timings of air inspiration and expiration are picked up will be described. Synchronization with patient's respiration which is the main feature of this invention is achieved through correct picking-up of the start timings of air inspiration and expiration. A deviation of even 0.1 second from real air inspiration and expiration will give the patient uncomfortable feelings with lost synchronization. In some case, effective respiration assistance becomes no more possible. Thus, respiration synchronization is an important function of this invention.

Detecting patient's respiration has been conducted heretofore with a temperature detection element, pressure detection element, a breast impedance detection element or the like. Particularly for a positive pressure artificial ventilator using a closed circuit, it is possible to synchronize the patient's respiration with ease by detecting a pressure within the closed circuit. ventilator as in the case of the present invention, it is not necessary to insert a tube within the windpipe of a patient so that patient's respiration is open to the atmospheric air. Detecting patient's respiration in such an open system has been conducted by detecting a change in temperature and pressure near the narises, or by measuring the breast impedance which varies with the motion of the chest wall. Such a method has been applied to a neonatal monitor which monitors the respiration rate and informing a stop of respiration, or to other apparatus.

The above-described conventional respiration detecting methods, however, although they are sufficient for detecting the presence or absence of respiration, are insufficient in that they cannot precisely pick up the start timings of air inspiration and expiration.

The present inventors have paid attention to the fact that a pyroelectric element generates an electromotive force proportional to a temperature change rate. The inventors have developed a new respiratory sensor for detecting the start timings of air inspiration and expiration, particularly with large temperature change, the sensor being disclosed in Japanese Patent Laid-open Publication JP-A-61-175496.

Figure 3:
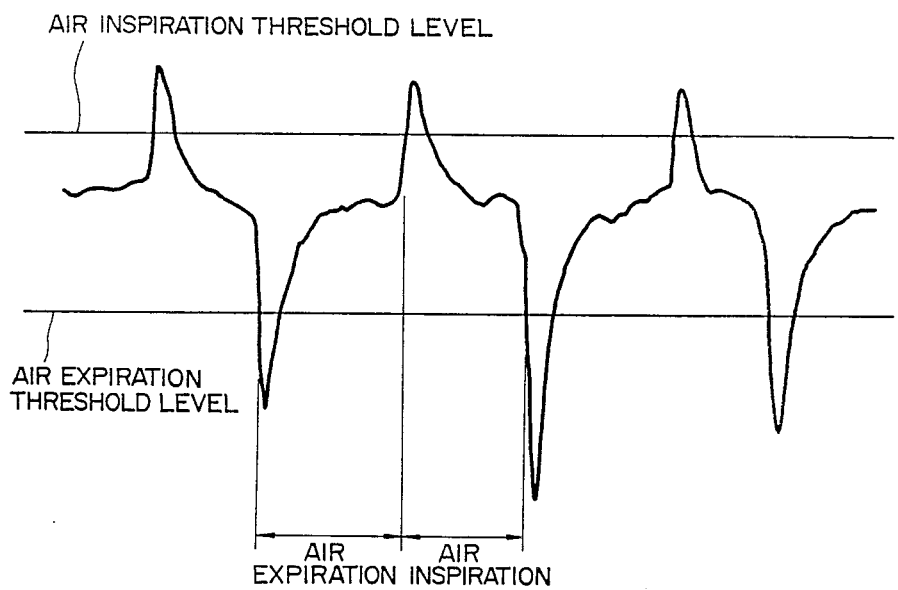
FIG. 3 is a graph showing an output waveform from the respiratory sensor used with this invention, and a triggering condition with constant threshold levels.

A pyroelectric element changes the value of spontaneous polarization of its ferroelectrics with a temperature change, and the surface charge thereof changes accordingly. If an external load is connected to the pyroelectric element, a pyroelectric current flows therethrough to restore the original surface charge without excessive or insufficient charge. No current flows thereafter until a temperature change occurs again. Thus, the pyroelectric element responds only when a temperature change occurs so that if such a pyroelectric element is used as a respiratory sensor, a differentiated waveform of respiration as shown in FIG. 3 can be obtained. Since this waveform has a sharp peak at the start of air inspiration or expiration, the start timings of air inspiration and expiration can be precisely picked up through triggering the waveform with suitable voltage levels. A pyroelectric element can generate a very high output as compared with other temperature sensitive elements such as thermisters. Therefore, it has a merit that amplification is not required, and the succeeding signal processing can be simplified.

Although it is not intended to be limited to the following material, a pyroelecrric element may use a single crystal such as lithium tantalate (LiTaO$_3$) and triglycine sulfate (TGS), a sintering substance made of such as lead titanate (PbTiO$_3$), lead zirconate titanate (PZT), or polyvinylidene, a high molecular ferroelectric substance such as polyvinylidene fluoride (PVDF), a composite substance made of a sintered ceramics powder and a plastic material, and other materials. The leading edge of an output of the respiratory sensor of this invention is dependent upon the temperature change rate of the pyroelectric element. Therefore, the thinner the thickness of the element is made to reduce the heat capacity, the better the response of the pyroelectric element becomes and the respiration timings can be picked up more sharply. Taking the above point of view into consideration, the following fact is led. Namely, the thickness of the element is 80 to 100 microns at most in the case of a single crystal or sintered ceramics. In addition, such an element is likely to be broken, and the workability of mounting the element to a support frame is poor. In contrast with the above, the process of manufacturing a film or sheet from, e.g., a high molecular ferroelectric simple substance or a composite substance of sintered ceramics powder and high molecular material, is easy so that an element whose thickness is several 10 microns or less can be easily made with excellent workability.

Figure 4:
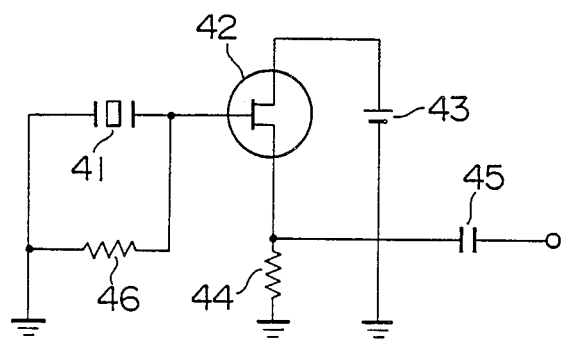
FIG. 4 is a circuit diagram of the respiratory sensor.

FIG. 4 is a circuit diagram showing an example of the electric circuit equivalent to the respiratory sensor used with this invention. The charge quantity to be generated on the pyroelectric element 41 by a temperature change is dependent upon the electric characteristics of the element such as an electrostatic capacitance, resistnace, pyroelectric factor, the size, the temperature change rate, and the like. The impedance of the element is generally as high as $10^8$ to $10^{11}$ ohm so that it is difficult to detect a change in charge of the element directly. Therefore, a recorder with an impedance converting buffer amplifier may be used, or a field effect transistor FET 42 is used to lower the impedance. The output impedance of FET 42 is determined by a resistor 44 which is preferably and ordinarily in the order of $10^3$ to $10^5$ ohm. A capacitor 45 is used for preferentially passing the high frequency component of an output signal, i.e., the signal component with large change rate. The waveform after passing the capacitor 45 changes in accordance with the quantity of its capacitance. Thus, the value of the capacitor 45 is determined so as to match the particular field of practical use. The capacitor 45 may not be used in some case. A gate resistor 46 is used to stabilize the bias of FET 42.

It is anticipated that lead wires interconnecting components, and circuit boards operate as antenas so that external noises will be inputted therethrough to obstruct to detecting correct temperature change. However, since an output of the pyroelectric element is large, if the circuit elements as shown in the embodiment of FIG. 7 including pyroelectric elements 71 and 72, FET 73, output resistor 74 and gate resistor 75 are assembled compactly on a single board, then external noise can be almost neglected. However, it is more perfect if the board 76 be covered with a conductive material to shield external electromagnetic waves (electromagnetic wave shielding). As the material of a main tube 77 shown in FIG. 7 which is integrally constructed, plastics, rubber, metal and the like may be used although not limited thereto. If conductive material such as metal is used, it advantageously serves also as an electromagnetic wave shielding material. However, the main tube 77 directly touches a patient's body so that the patient feels cold. Thus, it is preferable to use plastics, rubber or the like. If metal is used, the metal is preferably covered with plastics, rubber or the like. It is effective to give an electromagnetic shielding by using conductive plastics or rubber, or plastics with conductive material coated.

Figure 5:
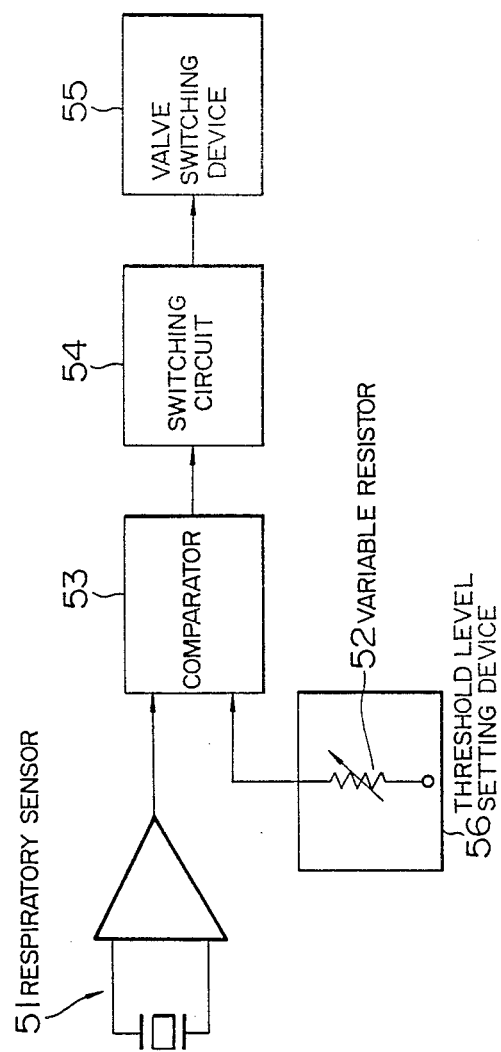
FIG. 5 is a block diagram of the respiration detection system.

FIG. 5 is a block diagram showing a respiration detection circuit. A signal from a respiratory sensor 51 is inputted to a comparator 53 to be compared with constant threshold levels which are adjustably supplied from a variable resistor 52 in a threshold level setting device 56. The starts of air inspiration and expiration are detected as the first points where the difference between the inputted signal and the threshold level becomes 0. Obviously, there are provided two threshold levels for air inspiration and expiration, which are properly adjusted by the variable resistor 52 to match a particular waveform of the respiratory sensor which waveform changes with each patient, respiration strength, speech or the like. In this manner, air inspiration and expiration can be picked up correctly. The start timing signals for air inspiration and expiration thus obtained are separated into an air inspiration start timing signal and an air expiration start timing signal by a switching circuit 54 such as a flip-flop circuit to operate upon a valve switching device 55 which drives magnetic valves.

Figure 2:
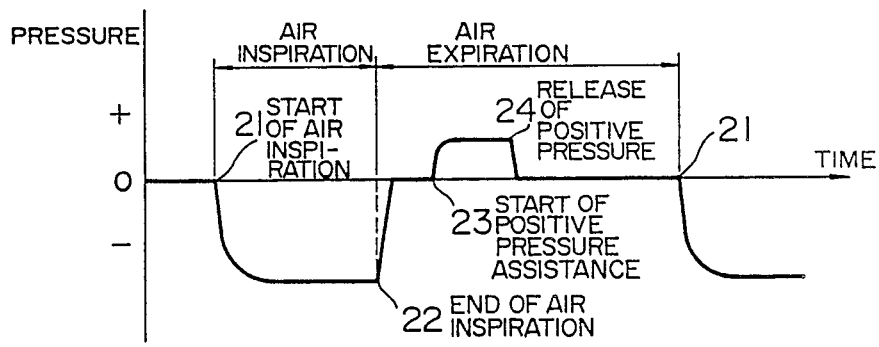
FIG. 2 is a graph showing a change of the pressure within the dome relative to respiration.

The valve switching method used with the artificial ventilator of this invention will now be described with reference to the accompanying drawings. FIG. 1 shows the piping system for air suction and exhaustion relative to the dome of the artificial ventilator according to an embodiment of this invention, and FIG. 2 shows a change of the dome internal pressure.

First, the dome internal pressure becomes negative pressure at the start 21 of air inspiration. In this state, the air exhaustion valve 12 is opened, the bypass valve 14 is closed, the bypass valve 16 is opened, the air suction valve 18 is closed, and the release valve 19 is closed. When the dome internal pressure reaches a predetermined value set by the negative pressure regulator 13, the bypass circuit of the negative pressure regulator 13 is made open to maintain the predetermined value without giving a greater negative pressure. Next, the negative pressure is temporarily released to the atmospheric pressure at the same time when the air inspiration terminates 22. In this state, the air exhaustion valve 12 is closed, the bypass valve 14 is opened, the bypass valve 16 is opened, the air suction valve 18 is closed, and the release valve 19 is opened. If it becomes necessary for patients such as with pulmonary emphysema, a positive pressure assistance for pushing down the patient thorax is performed by utilizing the air delivery pressure of the blower 4 and sending air into the dome through the air suction piping system 15. In this state, the air exhaustion valve 12 is closed, the bypass valve 14 is opened, the bypass valve 16 is closed, the air suction valve 18 is opened, and the release valve 19 is closed. The timing at the start 23 of the positive pressure assistance and the duration from the start 23 to the release 24 of the positive pressure are previously set by a timer so as to maintain a fixed time lapse from the start 21 of air inspiration. The maximum dome internal pressure during positive pressure assistance is adjusted by relieving air so as not to exceed a predetermined pressure set by the positive pressure regulator 17. In order to release the positive pressure, similar to the case where the negative pressure was released at the end 22 of air inspiration, the air exhaustion valve 12 is closed, the bypass valve 14 is opened, the bypass valve 16 is opened, the air suction valve 18 is closed, and the release valve 19 is closed.

The valve open/close states as described above are summarized in Table 1.

TABLE 1

| | Exhaustion Valve (12) | Bypass Valve (14) | Bypass Valve (16) | Suction Valve (18) | Release Valve (19) |
|---|---|---|---|---|---|
| Inspiration Start (Negative Pressure) | Open | Close | Open | Close | Close |
| Expiration Start (Release to Air) | Close | Open | Open | Close | Open |
| Positive Pressure Assistance | Close | Open | Close | Open | Close |
| Positive Pressure Release Release to Air) | Close | Open | Open | Close | Open |

During using an artificial ventilator, it is anticipated that there may occur a risk of apnea for a respiratory failure patient, a risk of detachment of the respiratory sensor because of some reason, or a risk of incorrect delivery of a signal from the respiratory sensor. In order to deal with such situations, it becomes more perfect if a backup system (I) or an air inspiration and expiration time setting system is adopted. According to the air inspiration and expiration system, the air inspiration and expiration times are previously set, and when an air inspiration signal is not obtained at the previously set air suction time, air suction is automatically made to start, i.e., the dome internal pressure is made negative, or contrarily when an air expiration signal is not obtained at the previously set air expiration time, air expiration is automatically made to start by releasing to the atmospheric pressure, while always preferentially synchronizing with the patient respiration. With such a backup system, it becomes possible to forcibly continue ventilation by the controlled respiration even if a patient becomes apnea, thus avoiding a patient's death. In addition, it becomes possible to continue the respiration assistance even if the respiratory sensor is detached. In such an abnormal situation, it is desirable to turn on a lamp or give an alarm to inform such effect.

A respiration assistance frequency selection system (II) is also effective for the case where it is intended not to use an artificial ventilator for a patient recovering from a disease or where an artificial ventilator is used for a patient with relatively slight disease. According to the respiration assistance frequency selection system, the spontaneous respiration of a patient is assisted not for all the respirations but once for every several respiration.

Figure 6A:
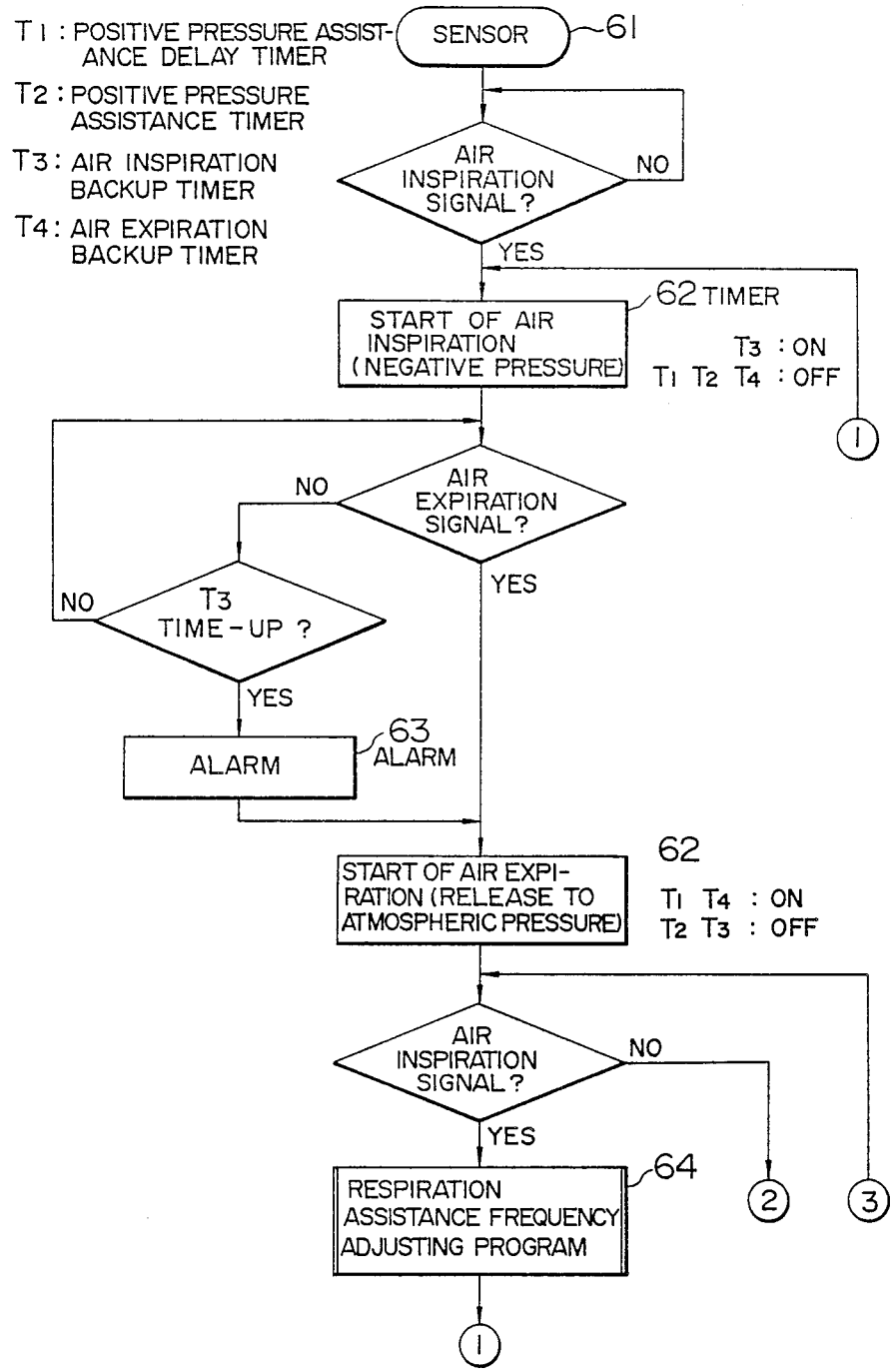
FIGS. 6A to 6C are flow charts illustrating the valve control program covering a respiration synchronizing backup (using the respiratory sensor) system and a respiration assistance frequency regulation system.
Figure 6B:
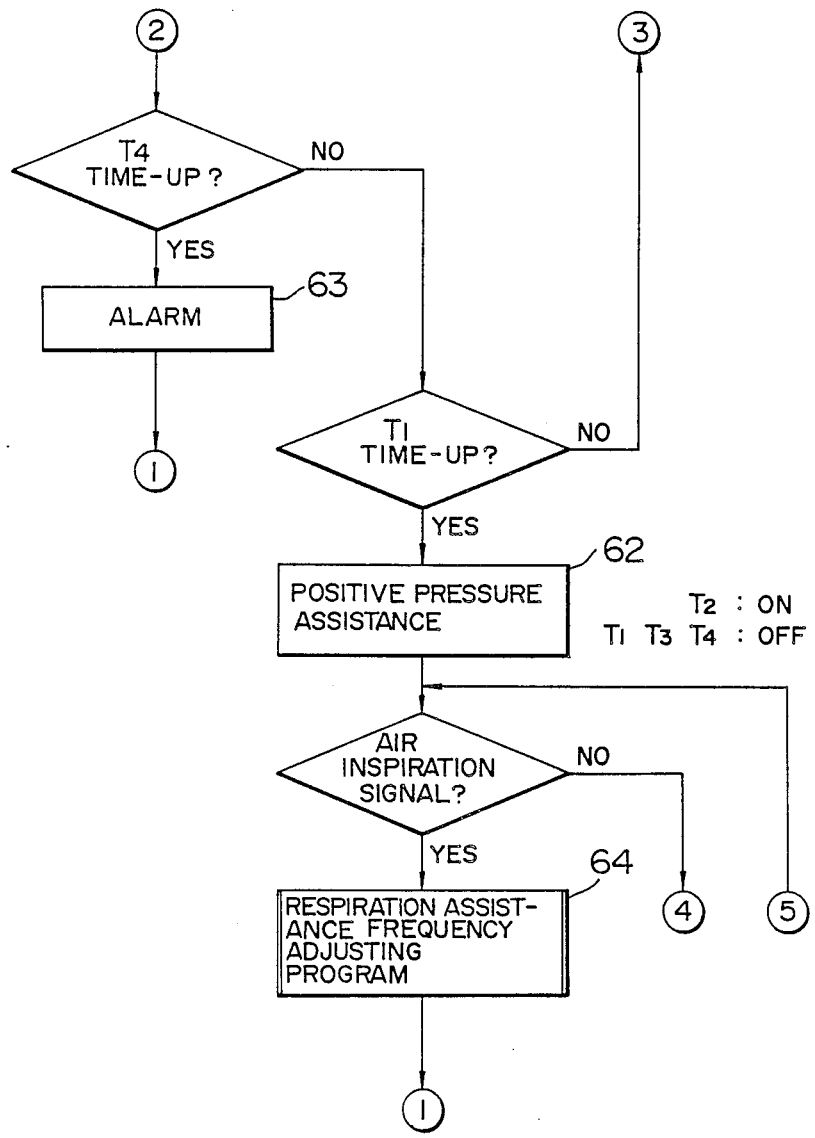
Figure 6C:
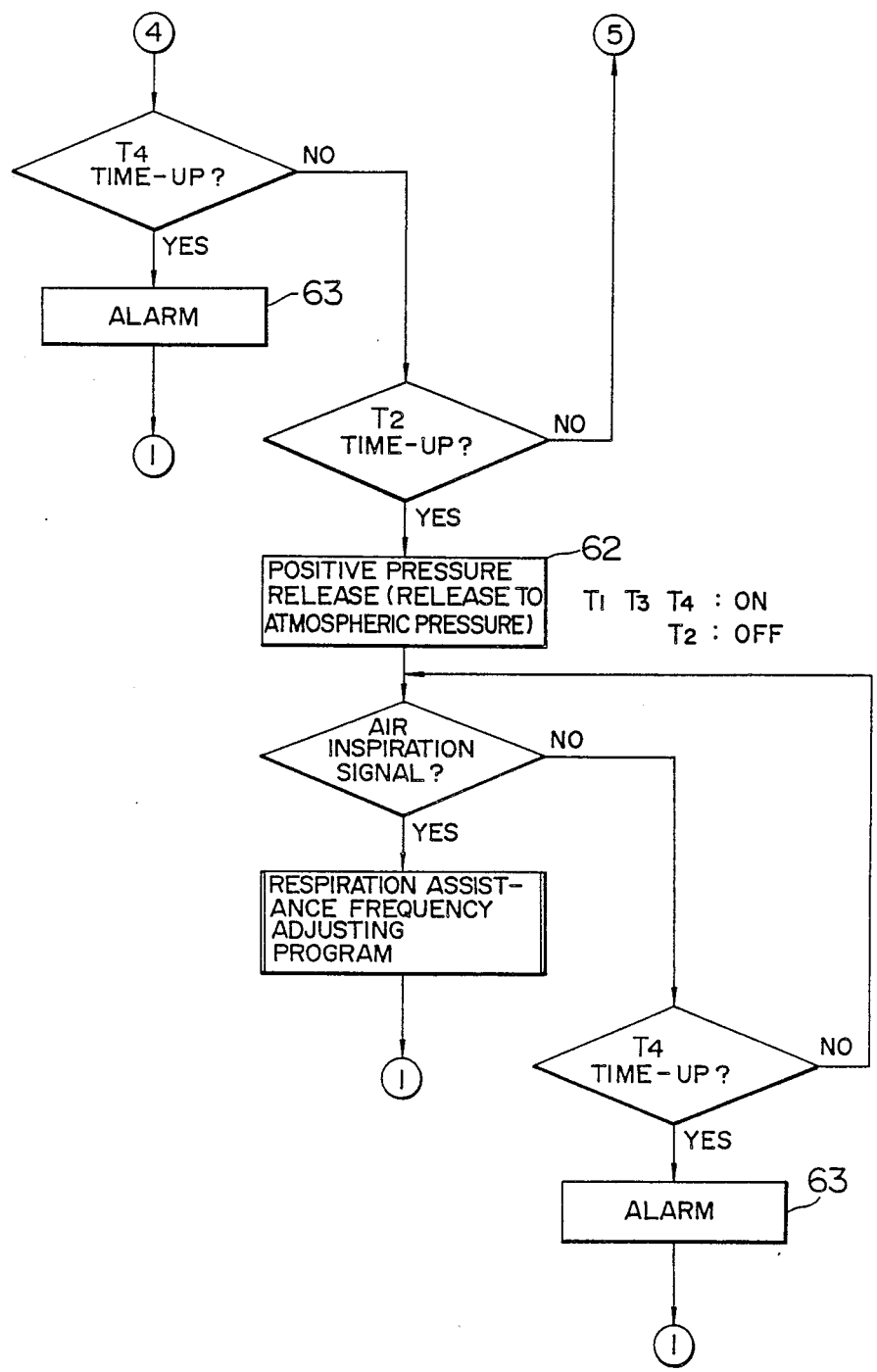

The backup system (I) and the respiration assistance frequency selection system (II) can be readily realized through execution and control by a microcomputer of a program shown in the flow charts of FIGS. 6A to 6C and stored in a read-only memory (ROM).

[I] (a) In the sensor mode using the respiratory sensor, air inspiration starts at the time when a first air inspiration signal is obtained from the sensor 61. The valves take the state of air inspiration start (negative pressure) shown in Table 1. An air inspiration backup timer T3 among timers 62 is caused to operate. The timer T3 is used for forcibly entering the air inspiration stage at its time-up if an air inspiration signal is not obtained at the previously set time. Such a case may be a respiration stop of a patient, a detachment of the respiratory sensor, or the like so that some notice to such effect is preferably given through an alarm 63.

Next, if an air inspiration signal is obtained or the timer T3 becomes time-up, the valves take the state of air expiration start (release to atmospheric air) shown in Table 1. A positive pressure assistance delay timer T1 for determining the time lapse when positive pressure assistance starts, and an air expiration backup timer T4 are caused to operate, whereas the timer T3 is made turned off. In the sensor mode, it is a fundamental rule to adopt a patient respiration priority so that if an air inspiration signal is obtained even before positive pressure assistance starts, the flow returns to (1) to perform the air inspiration stage.

[I] (b) If an air inspiration signal is not obtained, the flow advances to (2). If the timer T4 is not still time-up, then positive pressure assistance starts when the timer T1 becomes time-up. The valves take a state of positive pressure assistance shown in Table 1. In this state, if an air inspiration signal is obtained, an alarm is given and the air inspiration stage starts immediately (to advance to (1)). If positive pressure assistance is not necessary, the timer T1 is set longer than the timer T4 so that theoretically the positive pressure assistance stage cannot be entered but the negative pressure during air inspiration and the atmospheric pressure during air expiration are repeated.

[II] If the frequency of air inspiration assistance is to be adjusted, the respiration rate is counted with a respiration assistance frequency adjustment program 64 whereby respiration is assisted once for every several respirations by applying a negative pressure or a positive pressure, while maintaining the atmospheric pressure at the other respirations. The patient then takes an ordinary spontaneous respiration at the respirations other than the respiration assistance performed once for every several respirations.

[I] (c) If the air expiration state continues after the end of positive pressure assistance, the flow advances to (4). In particular, if an air inspiration signal is not still obtained, if the timer T4 is not time-up, and if the positive pressure assistance time timer t2 is time-up, then the positive pressure is released again to the atmospheric pressure for a preparatory stage for the air inspiration stage. The valves take a state of positive pressure release (to atmospheric pressure) shown in Table 1. Thereafter, the flow waits for an air inspiration signal or the time-up of the timer T4 to advance to the air inspiration stage (1).

[III] In addition to the above two systems [I] and [II], it is necessary to provide systems [III] and [IV]. In the system [III], only the air inspiration timings for example are synchronized with the spontaneous respiration of a patient to supply oxygen to the patient for the time set by a timer. In the system [IV], respiration is made by using timers only without a respiratory sensor, for a patient without spontaneous respiration such as a severe myasthenia patient. In this case, a more physiological forced respiration becomes possible if a deep breathing is given once for every several respirations by using another timer or another programming.

As described above, the several systems or modes [I] to [IV] can be selectively used by a switch in order to match a particular disease or condition of a patient, which is the distinctive feature of the present invention. The functions obtained by the systems [I] to [IV] can be optionally provided to an artificial ventilator. Obviously, it is not necessary to provide all the functions to a single artificial ventilator, but any combination of such functions can be provided in accordance with a particular filed of practical use.

Next, the respiratory sensor used with this invention will be described in detail in connection with its preferred embodiment.

The respiratory sensor uses pyroelectric elements, which is the distinctive feature of this invention as described previously. It is also one of the distinctive features to adopt the respiratory sensor of a nose cannula type which allows respiration assistance while performing oxygen inspiration.

Figure 7A:
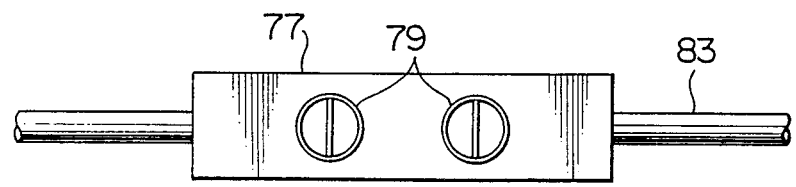
FIGS. 7A, 7B and 7C are the top view, cross sectional side view and bottom view showing the structure of the respiratory sensor.
Figure 7B:
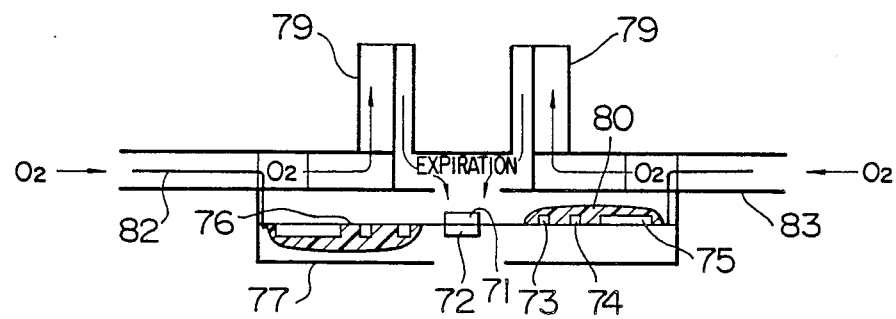
Figure 7C:
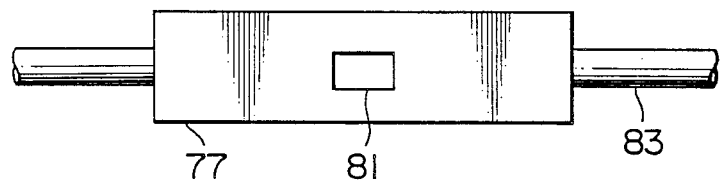

The circuit shown in FIG. 4 was made through assembly of pyroelectric elements 71 and 72, FET 73, gate resistor 75 and an output resistor 74 on a single board 76 as shown in FIGS. 7A, 7B and 7C. The components except the pyroelectric elements 71 and 72 are sealed with an epoxy-based liquid sealing resin 80 to avoid influence by external air or expired air. The board 76 is inserted into the main tube 77 to fixedly support it at opposite ends. A window 81 as shown in FIG. 7C is formed at the lower and middle plates of the main tube 77 at the position corresponding to that of the pyroelectric elements 71 and 72 to direct the expired air and external air.

Two tubes 79 to be inserted into narises are mounted on the upper plate of the main tube 77. Each tube has two lumina, one for oxygen gas and the other for communicating with the inside of the main tube 77 where the pyroelectric elements 71 and 72 are located. If the structure which allows oxygen gas to be directed to the pyroelectric elements 71 and 72 is adopted, oxygen gas flows toward the pyroelectric elements during the rest period of respiration, resulting in an incorrect detection signal. Therefore, this two lumen structure is important. The structure that the pyroelectric elements are mounted near the narises outside the main tube 77 may be adopted. However, some devise should be taken so as not to destroy the pyroelectric elements mounted outside.

In the above embodiment, the main tube 77 which houses the pyroelectric elements 71 and 72 and the other electric components is coated with conductive paint such as copper-based paint which is connected with a ground wire to shield external electromagnetic waves.

In the above embodiment, for the purpose of obtaining a better precision of signal detection, the air expiration detecting pyroelectric element 71 is mounted on the side of the naris inserting tube 79, and the air suction detecting pyroelectric element 72 on the side of external air (i.e., at the back of the board 76). In addition, two electric circuits shown in FIG. 4 are provided. However, a single electric circuit may be possible to detect both inspired and expired air. A pair of three-wire stranded leads are lead from the board 76 respectively for use as a pair of FET driver power sources, output signals and ground terminal, inserted into 83 of the nose cannula through which oxygen gas flows, and branched by Y-character shaped connectors to be connected to the detector circuit shown in FIG. 5.

The artificial ventilator according to the present invention can perform a physiological respiration assistance matching the patient physiological intention by synchronizing with the respiration timings of various respiratory failure patients. Therefore, an effort and pain in breathing in synchro with a conventional mechanical ventilation can be avoided. The artificial ventilator of this invention is particularly suitable for long term use and useful for rapid recovery of respiration function of an acute respiratory failure patient. Further, many auxiliary systems are used together to remedy a patient in accordance with a particular condition and disease of a patient, and maintain ventilation for avoiding a possible risk even if anything should happen. Such systems include a backup system or an air inspiration and expiration time setting system with respiration synchronization priority whereby a previously set, controlled respiration is repeated in the case of apnea or abnormal state of the respiratory sensor, a respiration assistance frequency adjustment system for a patient under recovery condition, a controlled respiration system for carrying out a controlled respiration using a timer for a respiratory muscle paralytic and the like systems. Therefore, the artificial ventilator of this invention is quite safe, durable for a long term comfortable use, and useful for medical industries.

EXAMPLE

A dome capable of covering up to the sides of thoraco-abdominal of a patient and serving as an artificial thoracic cavity was made of FRP using a gypsum mold. The portion where a patient body surface contact was attached with an urethane foam spongy, and the entirety thereof was coated with soft vinyl chloride resin.

A duct mounted at the apex of the dome was connected to the piping system as shown in FIG. 1, and the dome was mounted on the thorax of a subject (normal person). A blower having an air volume displacement of 0.86 $m^3$/min was used to exhaust air within the dome. The inner pressure reached from the atmospheric pressure to a negative pressure of $-15$ to $-20$ mm Hg after about 0.7 second. It was recognized that almost no air leakage from the dome bottom periphery was present.

The respiratory sensor having the structure as shown in FIG. 7 was attached to the narises of a subject to detect respiration. Inspired and expired air was triggered in the manner as shown in FIG. 3 to operate the valve switching device which is automatically controlled in accordance with the signals from the respiratory sensor. The valve switching device then could easily generate a negative pressure during air inspiration, normal pressure during air expiration, and positive pressure within the dome, in synchro with the patient respiration.

Further, after previously setting the air inspiration and expiration period information as for an air inspiration time of 1.7 second and an air expiration time of 3 seconds in the valve switching device, a subject temporarily stopped respiration or detached the respiratory sensor. In both the cases, it switched to a controlled respiration with air inspiration of 1.7 second and air expiration of 3 seconds.

Furthermore, by setting the respiration assistance frequency adjustment at $\frac{1}{2}$ or $\frac{1}{3}$, the respiration assistance was performed whereby a negative and positive pressures were applied once for every 2 or 3 spontaneous respirations of a patient, and during the other respirations the dome internal pressure was maintained at the atmospheric pressure to allow spontaneous respiration.

The respiratory sensor used was of the nose cannula type as shown in FIG. 7. It was confirmed that the respiration timings of a subject were precisely picked up using the respiratory sensor as above even while inspiring oxygen through the sensor or inspiring oxygen through the sensor and an oxygen mask attached to the subject.

We claim:

1. An artificial ventilator comprising:
 a dome made of hard material, said dome having an opening at the apex thereof for connection to an air duct and a fitting made of elastic material at the bottom periphery thereof;
 a blower adapted to be connected to said air duct for sucking and exhausting air in said dome;
 an air suction duct and an air exhaustion duct adapted to connect said dome and said blower together;
 a negative pressure regulator mounted on an exhaustion piping system;
 a positive pressure regulator mounted on a suction piping system;
 a pressure sensor for detecting a pressure within said dome;
 an exhaustion valve and a suction valve for controlling air exhaustion and suction;
 a release valve for releasing a negative or positive pressure into atmospheric air;
 a bypass valve for bypassing air when said air exhaustion valve or said air suction valve is closed;
 a valve switching device for controlling to open and close said air exhaustion valve, air suction valve, release valve and bypass valve; and
 a respiration detection system comprising a respiratory sensor including a pyroelectric element mounted at a passage of respiration air or near narises of a patient for detecting a temperature change rate at said passage or near said narises, and a respiration detection circuit for comparing a temperature change rate signal obtained by said pyroelectric element with a threshold value set at a variable resistor, detecting start timings of air expiration and air inspiration in accordance with the comparison result, and outputting a timing signal, said respiration detection system thereby controlling said valve switching device.

2. An artificial ventilator according to claim 1, wherein said backup system is selected to operate by said change-over switch and includes an air inspiration backup timer, air expiration backup timer, positive pressure assistance timer; and wherein
 said air inspiration backup timer with a previously set air inspiration time is caused to operate at the same time when air inspiration starts;
 if an air expiration signal is not obtained within said set time from said respiration detection system, than an air expiration signal is automatically generated;
 simultaneously with the start of air expiration, said positive pressure assistance delay timer having been set with a time lapse when a positive pressure is applied within the dome, and said air expiration backup timer having been set with an air expiration time are caused to operate;
 if an air inspiration signal is not obtained from said respiration detection system, within said set air expiration backup time and within said set positive pressure assistance delay time then a positive pressure assistance signal is generated to start positive pressure assistance and said positive pressure assistance timer having been set with a duration while positive pressure is being applied is caused to operate;
 if an air inspiration signal is not obtained within a remaining air expiration backup time, than an air inspiration signal is automatically generated; and if an air inspiration signal or an air expiration signal from said respiration detection system is obtained, then immediately on reception of said signal, an air inspiration or expiration stage starts.

3. An artificial ventilator according to claim 8, wherein said respiration assistance frequency setting system is selected to operate by said change-over switch, and uses, as a control signal of said valve switching device in order to apply a negative or positive pressure within said dome, a fraction of the start timing signals of air inspiration and expiration generated by said respiration detection system.

4. An artificial ventilator according to claim 8, wherein said inspiration timing tuning system is selected to operate by said change-over switch, and includes a timer for controlling said valve switching device, whereby an air inspiration excursion is set for the period from a generation of an air inspiration start timing signal from said respiration detection system to a time previously set by said timer; and an air expiration excursion is set for the period from the end of said air inspiration stage to the time the next air inspiration start timing signal is generated.

5. An artificial ventilator according to claim 4, wherein said respiratory sensor comprises said pyroelectric element, a field effect transistor, and a resistor element, and the entirety of said respiratory sensor is covered with a conductive material layer to shield said sensor from external electromagnetic waves.

6. An artificial ventilator according to claim 8, said change-over switch, and includes timer means presetting an air inspiration time and an air expiration time in order to control said valve switching device.

7. An artificial ventilator according to claim 6, comprising further timer means for controlling said valve switching device in order to cause a deep breathing once for every several to tens respirations, by an additional timer or program means other than said timer.

8. An artificial ventilator comprising:

a dome made of hard material, said dome having an opening at the apex thereof for connection to an air duct and a fitting made of elastic material at the bottom periphery thereof;

a blower adapted to be connected to said air duct for sucking and exhausting air in said dome;

an air suction duct and an air exhaustion duct adapted to connect said dome and said blower together;

a negative pressure regulator mounted on an exhaustion piping system;

a positive pressure regulator mounted on a suction piping system;

a pressure sensor for detecting a pressure within said dome;

an exhaustion valve and a suction valve for controlling air exhaustion and suction;

a release valve for releasing a negative or positive pressure into atmospheric air;

a bypass valve for bypassing air when said air exhaustion valve or said air suction valve is closed;

a valve switching device for controlling to open and close said air exhaustion valve, air suction valve, release valve and bypass valve;

a sensor mode system, a backup system, a respiration assistance frequency setting system, an inspiration timing tuning system and a timer dependent respiration adjusting system, said sensor mode system being adapted to control said valve switching device by a respiration detection system which comprises a respiratory sensor including a pyroelectric element mounted at a passage or respiration air or near said narises of a patient for detecting a temperature change rate at said passage or near said narises, and a respiration detection circuit for comparing a temperature change rate signal obtained by said pyroelectric element with a threshold value set at a variable resistor, detecting start timings of air expiration and air inspiration in accordance with the comparison result, and outputting a timing signal;

ROM storing program for operating at least one of said sensor mode system, backup system, said inspiration assistance frequency setting system, said inspiration timing tuning system and said timer dependent respiration adjusting system; and a change-over switch for selecting at least one of said systems to be operated.

9. An artificial ventilator according to claim 8, wherein said respiratory sensor comprises said pyroelectric element, a field effect transistor, and a resistor element, and the entirety of said respiratory sensor is covered with a conductive material layer to shield said sensor from external electromagnetic waves.

10. An artificial ventilator according to claim 6, further comprising program means for controlling said valve switching device in order to cause a deep breathing once for every several to tens respirations.

* * * * *